United States Patent [19]

Liptak

[11] Patent Number: 4,895,142

[45] Date of Patent: Jan. 23, 1990

[54] ARM SLING

[76] Inventor: Nancy Liptak, 7997 Pettibone Rd., Bainbridge Township, Cuyahoga County, Ohio 44022

[21] Appl. No.: 214,034

[22] Filed: Jun. 30, 1988

[51] Int. Cl.[4] ............................. A61F 5/37; A61F 5/40
[52] U.S. Cl. ............................. 128/94; 128/DIG. 19; 128/878; 128/165
[58] Field of Search ............... 128/94, 165, 82, 85, 128/878, 881, DIG. 19

[56] References Cited

U.S. PATENT DOCUMENTS

| | | | |
|---|---|---|---|
| 1,745,446 | 2/1930 | Payne | 128/94 |
| 2,539,677 | 1/1951 | Teare | 128/94 |
| 2,549,703 | 4/1951 | New | 128/94 |
| 3,371,663 | 3/1968 | Apgar | 128/94 |
| 3,433,221 | 3/1969 | Kendall et al. | 128/94 |
| 4,437,459 | 3/1984 | Slavetskas | 128/94 |
| 4,497,316 | 2/1985 | Lilla | 128/94 |
| 4,510,928 | 4/1985 | Ackley | 128/94 |
| 4,550,724 | 11/1985 | Berrehail | 128/94 X |
| 4,733,658 | 3/1988 | Ruthven, Jr. | 128/94 |

FOREIGN PATENT DOCUMENTS 188606  9/1907  Fed. Rep. of Germany ........ 128/94

Primary Examiner—Mickey Yu
Assistant Examiner—Kevin G. Rooney
Attorney, Agent, or Firm—Pearne, Gordon, McCoy & Granger

[57] ABSTRACT

An arm sling is made from a length of material comprising a sleeve portion and a back portion which is a continuation of one side of the sleeve portion. The sleeve portion supports the arm in a diagonal position across the chest. The back portion extends diagonally across the back and is adjustably attached to the end of the sleeve portion at the opposite shoulder.

4 Claims, 1 Drawing Sheet

ARM SLING

BACKGROUND OF THE INVENTION

1. Field of the Invention

This invention relates to medical appliances, and more particularly to arm slings.

2. Description of the Prior Art

Prior art arm slings have traditionally provided a trough for insertion of the forearm, and a strap connecting the ends of the trough to support the sling around the back of the wearer's neck. Examples of slings having such a design and variations thereof include U.S. Pat. No. 980,464, issued to Wermuth; U.S. Pat. No. 2,875,754, issued to Messer; U.S. Pat. No. 3,433,221, issued to Kendall et al.; U.S. Pat. No. 4,220,149, issued to Mims; U.S. Pat. No. 4,372,301 issued to Hubbard et al.; U.S. Pat. No. 4,510,928, issued to Ackley; U.S. Pat. No. 4,622,961 issued to Christensen.

The designs of prior art arm slings have had several problems associated with them. Because the slings were simply supported over the neck, they allowed the arm to swing outwardly when the wearer bent forward. This may be uncomfortable to the wearer and may subject the arm to bumping as the wearer moves about. While some prior art arm slings held the arm in a relatively comfortable position, the comfort provided by such slings could still be improved upon. Most previous arm slings were also secured over the shoulder with a thin strap causing pressure and discomfort on the neck and shoulder after the sling was worn for an extended period of time. The arm position provided by most previous arm slings also promoted swelling in the hand, since the hand was often maintained at a position below the elbow.

The prior art arm sling also usually included one or more items of hardware, such as metallic attachment pieces, which made the slings difficult to wash and which could cause discomfort to the wearer, especially if the wearer bumped his or her arm near the location of one of these items of hardware. The slings were designed for either the left or right arm, but not both, so that a sling designed for the left arm was useless if a right arm sling was needed. These slings were often bulky, presenting an unattractive appearance and making it difficult to wear coats or other outer garments comfortably. Furthermore, the hand was usually exposed, which may be uncomfortable particularly during cold weather. In addition, prior art arm slings were typically made of a plurality of individual pieces which are assembled together, making the slings relatively expensive to fabricate.

SUMMARY OF THE INVENTION

The arm sling of the present invention overcomes many of the problems of the prior art arm sling designs and provides other advantages that have not been realized before now. The present invention provides an arm sling having an exceptionally simple design which advantageously supports the forearm in a raised position with the arm extending diagonally across the body. The position in which the sling of the present invention holds the arm is more natural for many wearers, and thus makes the use of an arm sling for an extended period of time more bearable for most people.

The arm sling design of the present invention provides better support, and makes the arm less prone to swinging outwardly when the wearer bends forward. This design also provides a more comfortable position for the wearer with the arm next to the body and makes it easier to wear a coat or other outer garments. The arm sling design of the present invention also eliminates the thin shoulder straps of the prior art sling designs, making the sling more comfortable when worn for an extended period of time. Furthermore, the arm position provided by the arm sling of the present invention promotes a raised position for the arm which minimizes or reduces swelling in the hand.

The simplicity of the design of the arm sling of the present invention allows it to be quickly fitted to the wearer. The arm sling design is the same for either arm, so that it is not necessary to provide different slings for the right and left arms. The arm sling of the present invention is easily adjustable, facilitating the use of the sling by a variety of wearers. The entire sling is soft without hardware or other hard items which could cause discomfort if the wearer bumps his or her arm. In addition, the sling completely covers the hand, providing protection and warmth in cold weather. Furthermore, the sling can also be made from a single length of material, thus making the sling relatively inexpensive to produce.

These and other advantages are provided by the arm sling of the present invention which comprises an elongated length of material having a first end and a second end. The length comprises a front tubular sleeve portion extending from the first end to a intermediate position. The sleeve portion is open at the intermediate position for insertion of a forearm up to the elbow. The sleeve portion is adapted for supporting the forearm diagonally across the front of the body toward the opposite shoulder. The length also includes a back portion comprising a continuation of one side of the sleeve portion. The back portion extends from the intermediate portion to the second end. The back portion is adapted to extend from the elbow diagonally across the back of the opposite shoulder. The arm sling also comprises attachment means for attaching the first end to the second end over the opposite shoulder.

DETAILED DESCRIPTION OF THE PREFERRED EMBODIMENT

Figure 1:
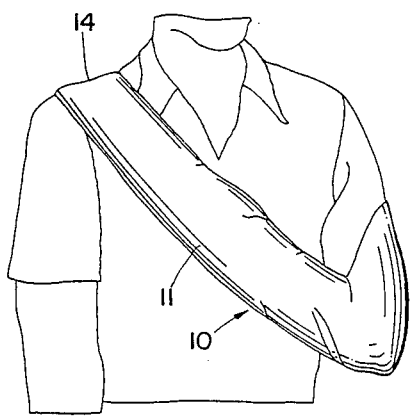
FIG. 1 is a front view of a patient wearing the arm sling of the present invention.
Figure 2:
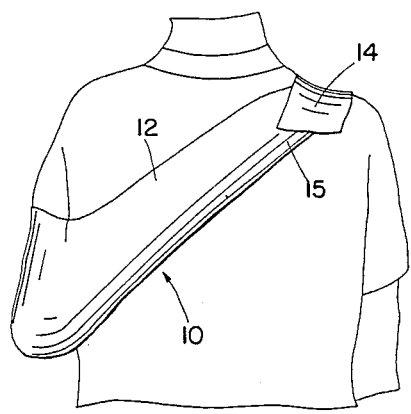
FIG. 2 is a rear view of the patient wearing the arm sling of FIG. 1.

Referring more particularly to the drawings and initially to FIG. 1, there is shown the arm sling 10 of the present invention as worn. The arm sling 10 comprises a front sleeve portion 11 which supports the wearer's forearm in a diagonal position across the front of the torso with the hand elevated. The forearm is inserted into the tubular sleeve portion 11 up to the elbow, so that the sleeve portion should be sufficiently wide and long to accommodate the forearms of most patients, including an arm cast if necessary. The sleeve portion 11 extends from the elbow across the chest to the opposite shoulder. As shown in FIG. 2, the arm sling 10 also comprises a back portion 12 which extends diagonally across the wearer's back. The back portion 12 comprises a continuation of a portion of the sleeve portion 11, and extends from the wearer's elbow to the opposite shoulder in use.

When the arm sling 10 is worn, the end 14 of the sleeve portion 11 adjacent to the wearer's hand and the end 15 of the back portion 12 are attached together at the opposite shoulder to support the arm in the sling. The attachment of the end 14 of the sleeve portion 11 to the end 15 of the back portion 12 may be made by any suitabe means, the preferred attachment means being Velcro fasteners, with fastening strips being sewed or otherwise attached to each of the ends 14 and 15 of the sling 10.

Figure 3:
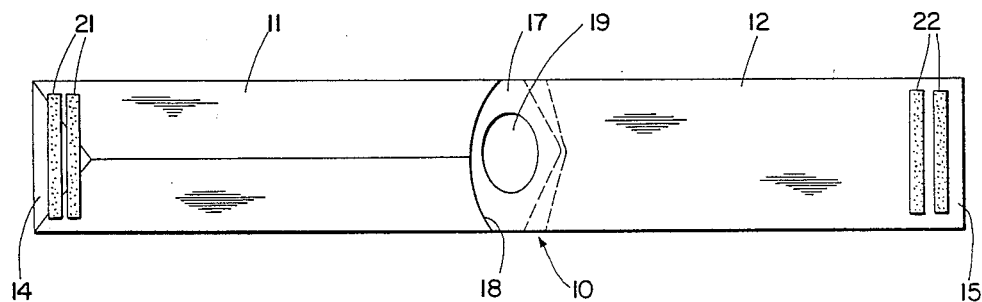
FIG. 3 is an elevational view of the arm sling of FIGS. 1 and 2 prior to use.

The fabrication of the arm sling 10 of the present invention may be seen with reference to FIG. 3. The arm sling 10 provides an exceptionally simple design comprising a length of durable fabric with the sleeve portion 11 extending from an intermediate location 17 to one end 14 of the length. The front sleeve portion 11 is preferably closed at the outer end 14, but it may be open at the end 14 to accommodate access to the wearer's hand. At the intermediate location 17 is an opening 18 in the sleeve portion 11 for insertion of the wearer's forearm. The back portion 12 extends from the sleeve portion 11 at the intermediate location 17 and extends to the other end 15 of the sling 10. The back portion 12 thus forms a continuation of one side of the sleeve portion 11, so that the entire sling 10 may be made of a single length of material. If desired, a pad 19 may be provided adjacent to the opening 18 for comfortable support of the wearer's elbow.

Velcro strips 21 and 22 are provided at each of the ends 14 and 15 of the arm sling 10. As shown in FIG. 3, Velcro strips 21, e.g., of the "loop" type, are provided on the sleeve portion end 14, and Velcro strips 22, e.g., of the "hook" type, are provided on the back portion end 15. Preferably, longitudinally extending Velcro strips 21 and 22, or a plurality of traverse strips are provided so that the length of the sling 10 may be adjustable. While the strips 21 and 22 are shown in FIG. 3 as being on the same side of the sling, it may be preferable to provide one of the strips 21 or 22 on the opposite side of the sling from the other strip, so that the ends 14 and 15 of the sling can be more easily attached when the sling is fitted on the wearer.

The arm sling 10 of the present invention can be quickly fitted to the wearer. The wearer first inserts his or her forearm into the opening 18 and rests the elbow on the pad 19. The forearm is then positioned diagonally across the wearer's chest with the end 14 positioned on the opposite shoulder, and the back portion 12 is pulled diagonallly across the wearer's back with the end 15 at the opposite shoulder. The attachment strips 21 and 22 are then attached together at the opposite shoulder to connect the sleeve portion end 14 to the back portion end 15. The wearer's shoulder and neck and back support the arm in the sling 10.

The arm sling 10 is easily adjustable to accommodate the proportions of the wearer, and to allow the wearer to have the arm positioned in the most comfortable position. The height of the wearer's hand and thus the elevation of the arm may be adjusted by adjusting the point of attachment of the ends 14 and 15. As the sling is increased in length, the elevation of the hand is lowered. If the length of the sling is reduced, the elevation of the hand is raised.

Because the point of attachment of the sling is very close to the wearer's hand and because the position of the elbow is stabilized, the sling is less likely to swing forward if the wearer bends forward. In addition, the raised position of the arm is more natural for many wearers and is thus more comfortable.

Various modifications to the basic arm sling design are possible. For example, the sleeve portion 11 may be made of a knit fabric or elastic material permitting it to expand in order to better accommodate the larger size of an arm cast. Alternatively, the sleeve portion 11 may be provided with a longitudinally extending elastic insert so that the size of the sleeve portion can be expanded to receive an arm cast.

While the invention has been shown and described with respect to a particular embodiment thereof, this is for the purpose of illustration rather than limitation, and other variations and modifications of the specific embodiment herein shown and described will be apparent to those skilled in the art all within the intended spirit and scope of the invention. Accordingly, the patent is not to be limited in scope and effect to the specific embodiment herein shown and described nor in any other way this is inconsistent with the extent to which the progress in the art has been advance by the invention.

What is claimed is:

1. An arm sling, which comprises:
    a single elongated unitary length of material having a first end and a second end and an intermediate location therebetween,
        one portion of the length extending from the first end to the intermediate location being generally rectangular with a first width sufficiently wide to permit the longitudinal sides of the portion to be connected together to form a front tubular sleeve portion, the sleeve portion having an opening at the intermediate location for insertion of a forearm into the sleeve portion up to the elbow while leaving the arm above the elbow substantially uncovered, the sleeve portion being adapted for enveloping the forearm and supporting the forearm diagonally across the front of the body toward the opposite shoulder, and the other portion of the length extending from the intermediate location to the second end having a second width that is approximately less than half as wide as the first width to form a back portion, the back portion comprising a continuation of one side of the sleeve portion, the back portion immediately adjacent to the opening in the sleeve portion alone providing a support for the elbow, the back portion adapted to extend from the elbow diagonally across the back to the opposite shoulder; and
    attachment means for attaching the first end to the second end over the opposite shoulder.

2. An arm sling as defined in claim 1, wherein the attachment means are adjustable.

3. An arm sling as defined in claim 1, comprising in addition a pad at the intermediate location for resting the elbow.

4. An arm sling as defined in claim 1, wherein the sleeve portion is expandable to accommodate an arm cast.

* * * * *

UNITED STATES PATENT AND TRADEMARK OFFICE
CERTIFICATE OF CORRECTION

PATENT NO. : 4,895,142
DATED : January 23, 1990
INVENTOR(S) : Nancy Liptak

It is certified that error appears in the above-indentified patent and that said Letters Patent is hereby corrected as shown below:

Column 3, line 9, "suitabe" should read --suitable--

Signed and Sealed this

Eighth Day of March, 1994

Attest:

BRUCE LEHMAN

Attesting Officer

Commissioner of Patents and Trademarks